United States Patent [19]

Bru-Magniez et al.

[11] Patent Number: 5,219,839
[45] Date of Patent: Jun. 15, 1993

[54] ADENOSINE DERIVATIVES, THEIR METHODS OF PREPARATION AND PHARMACEUTICAL COMPOSITIONS IN WHICH THEY ARE PRESENT

[75] Inventors: Nicole Bru-Magniez, Paris; Timur Gungör, Rueil; Jean-Marie Teulon, La Celle Saint Cloud, all of France

[73] Assignee: Laboratories UPSA, Agen, France

[21] Appl. No.: 844,778

[22] Filed: Mar. 2, 1992

[30] Foreign Application Priority Data

Jan. 31, 1992 [FR] France .................. 92 01113

[51] Int. Cl.$^5$ ............... C07H 19/167; A61K 31/70
[52] U.S. Cl. ..................... 514/46; 536/27.22
[58] Field of Search ................ 514/46; 536/26

[56] References Cited

U.S. PATENT DOCUMENTS

| | | | |
|---|---|---|---|
| 4,167,565 | 9/1979 | Stein et al. | 514/46 |
| 5,023,244 | 6/1991 | Goto et al. | 514/46 |

FOREIGN PATENT DOCUMENTS

| | | |
|---|---|---|
| 222330 | 5/1987 | European Pat. Off. . |
| 232813 | 8/1987 | European Pat. Off. . |
| 251339 | 1/1988 | European Pat. Off. . |
| 423776 | 4/1991 | European Pat. Off. . |
| 423777 | 4/1991 | European Pat. Off. . |
| WO86/00310 | 1/1986 | PCT Int'l Appl. . |
| WO88/03147 | 5/1988 | PCT Int'l Appl. . |
| WO88/03148 | 5/1988 | PCT Int'l Appl. . |
| 2199036 | 6/1988 | United Kingdom . |

OTHER PUBLICATIONS

"Journal of Medicinal Chemistry", vol. 28, No. 10, 1985, Washington US, pp. 1636–1643, S. Kusachi et al.

*Primary Examiner*—Johnnie R. Brown
*Assistant Examiner*—L. Eric Crane
*Attorney, Agent, or Firm*—Dennison, Meserole, Pollack & Scheiner

[57] ABSTRACT

The present invention relates to the derivatives of the formula

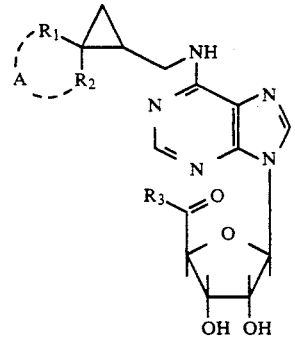

Formula (I)

and the corresponding enantiomers and diastereoisomers and, if appropriate, their addition salts, and to their use in therapeutics, especially in the central nervous system as analgesics, anticonvulsants, antiepileptics, anxiolytics, antidepressants and neuroprotectors, and in the cardiovascular system as antiarrhythmics, antihypertensives and platelet aggregation inhibitors.

8 Claims, No Drawings

ADENOSINE DERIVATIVES, THEIR METHODS OF PREPARATION AND PHARMACEUTICAL COMPOSITIONS IN WHICH THEY ARE PRESENT

The present invention relates, by way of novel products, to the adenosine derivatives of general formula (I) below and the corresponding enantiomers and diastereoisomers and, if appropriate, their addition salts, in particular the pharmaceutically acceptable addition salts.

The compounds in question have a very valuable pharmacological profile insofar as they are active on the one hand in the central nervous system, where they possess especially analgesic properties but also anticonvulsant, antiepileptic, anxiolytic, antidepressant and neuroprotective properties, and on the other hand in the cardiovascular system, where they possess especially antiarrhythmic, antihypertensive and platelet aggregation inhibiting properties.

The present invention further relates to the method of preparing said products, to the synthesis intermediates and to the application of these products in therapeutics.

These adenosine derivatives have general formula (I):

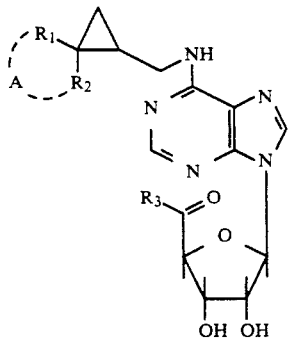

Formula (I)

in which $R_1$ and $R_2$, which are identical or different, are an aromatic ring selected from:
- a phenyl or naphthyl radical which is unsubstituted or monosubstituted or polysubstituted by a halogen atom or a trifluoromethyl, nitro, hydroxyl, thio, lower alkyl, lower O-alkyl or lower S-alkyl group, and
- a heteroaromatic group having from 5 to 7 atoms and containing 1 to 3 heteroatoms selected from nitrogen, oxygen and sulfur, which is unsubstituted or monosubstituted or polysubstituted by a halogen atom or a trifluoromethyl, nitro, hydroxyl, thio, lower alkyl, lower O-alkyl or lower S-alkyl group, it being possible for the rings $R_1$ and $R_2$ to be joined together by a single bond, a CH=CH or —CH$_2$—CH$_2$— group or else a group —B—CH$_2$, B being a heteroelement such as oxygen, nitrogen or sulfur; and $R_3$ can be a group $OR_4$ or $NHR_4$, $R_4$ being a hydrogen atom, a lower alkyl radical, a $C_3$-$C_7$ cycloalkyl radical, a lower alkyl chain possessing an alcohol or thiol functional group, or else a group —(CH$_2$)$_n$—NR$_5$R$_6$, n being an integer from 1 to 4 and $R_5$ and $R_6$ simultaneously being a lower alkyl radical or it being possible for $R_5$ and $R_6$ to form, together with the nitrogen atom to which they are attached, a ring of 5 to 7 atoms which can contain one to three heteroatoms selected from oxygen, sulfur or nitrogen.

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$-$C_7$ cycloalkyl radical is understood as meaning a saturated cyclic radical, preferably a cyclopropane, cyclobutane, cyclopentane, cyclohexane or cycloheptane radical.

Halogen is understood as meaning a chlorine, bromine, iodine or fluorine atom.

Lower alkyl chain possessing an alcohol or thiol functional group is understood as meaning a lower alkyl chain in which one of the hydrogen atoms has been substituted by a hydroxyl or thio group. Such a chain is for example the 1-hydroxy-2-methylpropan-2-yl chain.

A heteroaromatic group having from 5 to 7 carbon atoms and containing 1 to 3 heteroatoms selected from nitrogen, oxygen and sulfur is for example a furan, pyrrole, thiophene, pyran, pyridine, oxazole, thiazole, pyrazole or pyrimidine group.

In general formula (I), the letter A symbolizes the bond which may be present between the rings $R_1$ and $R_2$.

When they are joined together, the rings $R_1$ and $R_2$ form an ortho-fused tricyclic group with the carbon atom to which they are otherwise joined.

An example of such an ortho-fused tricyclic group is the 5H-fluorene, 5H-dibenzo[a,d]cycloheptene or 10,11-dihydro-5H-dibenzo[a,d]cycloheptene group.

According to one feature of the invention, $R_1$ and $R_2$, which are identical or different, are an aromatic ring selected from:
- a phenyl radical which is unsubstituted or monosubstituted or polysubstituted by a halogen atom, and
- a pyridyl radical, preferably pyrid-3-yl, it being possible for the rings $R_1$ and $R_2$ to be joined together by a single bond or a CH=CH or CH$_2$—CH$_2$ group; and $R_3$ is a group $NHR_4$, $R_4$ being a hydrogen atom, a lower alkyl radical or a lower alkyl chain possessing an alcohol functional group.

According to one variant, $R_1$ is a phenyl.
According to one variant, $R_2$ is a phenyl.
According to another variant, A is absent.
According to another variant, A is a single bond.
According to one variant, $R_1$ is a parafluorophenyl.
According to another variant, $R_2$ is a parafluorophenyl.
According to one variant, $R_3$ is an N-ethylamine radical.
According to another variant, $R_3$ is an N-cyclopropylamine radical.

The particularly preferred compounds of the invention are selected from the derivatives of the formulae

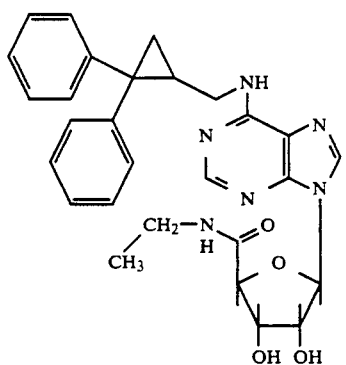

(+) isomer, (−) isomer and racemate

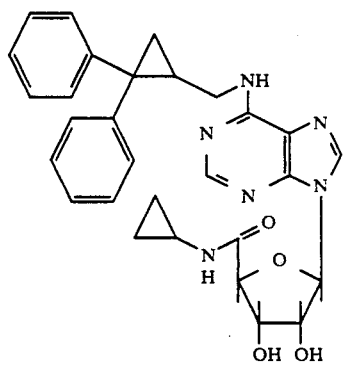

(−) isomer and racemate

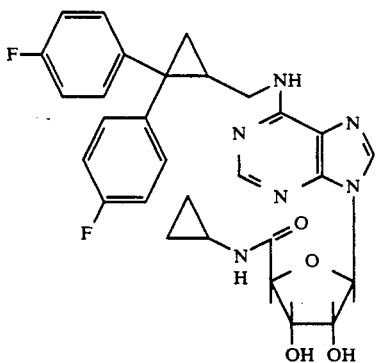

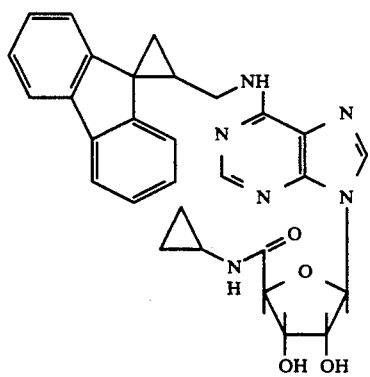

According to the invention, the compounds of formula (I) may be synthesized in the following manner:
Reaction of an amine of formula (II):

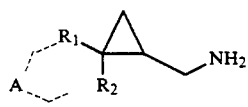

Formula (II)

in which $R_1$, $R_2$ and A are as defined above, with the 6-halogenopurine ribosides of formula (III):

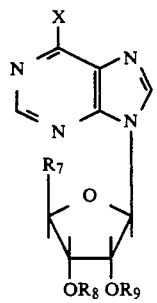

Formula (III)

in which X is a halogen atom, preferably chlorine or bromine, $R_7$ can be the group $COR_3$, $R_3$ being as defined above, or the $CH_2OH$ group, and $R_8$ and $R_9$ are protecting groups for the alcohol functional group, such as, for example, an acetyl, a benzoyl or a benzyl, or can together form another protecting group, for example of the dioxolan structure, in a solvent such as, for example, an alcohol or an aprotic solvent such as dimethylformamide, in the presence of a base such as triethylamine, pyridine or sodium, potassium or calcium carbonate, or else in the presence of two equivalents of the amine of formula (II), at a temperature of between 20° and 140° C., will give the compounds of formula (IV):

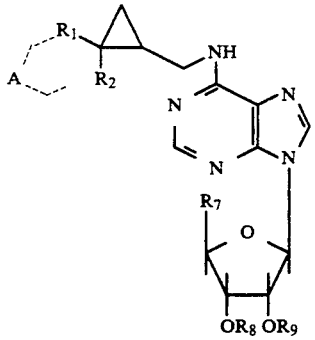

Formula (IV)

in which $R_1$, $R_2$, $R_7$, $R_8$, $R_9$ and A are as defined above.
In the case where the radical $R_7$ is the $CH_2OH$ group, it will be possible to oxidize it with chromium trioxide in accordance with the method described by:

R. R. SCHMIDT and H. J. FRITZ, Chem. Ber., 1970, 103, 1867, or with potassium permanganate in the presence of aqueous ammonia according to:

P. J. HARPER and A. HAMPTON, J. Org. Chem., 1970, 35, n° 5, 1688.

The resulting ribouronic acid will then be converted to the acid chloride by reaction with thionyl chloride, for example, and then to an amide by reaction with an amine or to an ester by reaction with an alcohol in accordance with the methods known to those skilled in the art; deprotection of the secondary alcohols $OR_8$ and $OR_9$ may be carried out in accordance with different methods, namely in a basic medium such as ammoniacal alcohol, or in an acid medium such as a normal hydrochloric acid solution or a formic acid solution, at temperatures varying from 0° to 70° C. depending on the nature of the protecting groups.

These reaction sequences make it possible to convert the derivatives of formula (IV) to derivatives of formula (I).

The compounds of formula (II) may be obtained by reducing the compounds of formula (V):

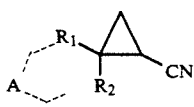

Formula (V)

in which $R_1$, $R_2$ and A are as defined above.

This reduction can be carried out in the presence of reducing agents such as $LiAlH_4$, $LiAlH_4/AlCl_3$, $AlH_3$, $BH_3$ etc., in the presence of solvents such as ether, THF or an ether/THF mixture, at temperatures of between 0° and 30° C. It is also possible to use catalytic hydrogenation under pressure or at atmospheric pressure, in the presence of a base such as ammonia, in a solvent such as methanol.

The derivatives of formula (V) can be obtained by any one of the methods of synthesizing cyclopropanes which are known in the literature, such as, for example, the Simmons-Smith reaction, J. Am. Chem. Soc., 81, p. 4256 (1959), or by the method of converting epoxides with certain phosphorus ylides [Denney, Vill and Boskin, J. Am. Chem. Soc., 84, p. 3944 (1962)], or else by the use of γ-halogenated borane compounds [Brown and Rhodes, J. Am. Chem. Soc., 91, p. 2149 and p. 4306 (1969)].

One particular method consists in proceeding via diazirines, which can give carbenes; reaction of these with vinylic compounds yields cyclopropane derivatives.

Thus the derivatives of formula (V) can be obtained in accordance with the following reaction scheme, starting from ketones of formula (VI):

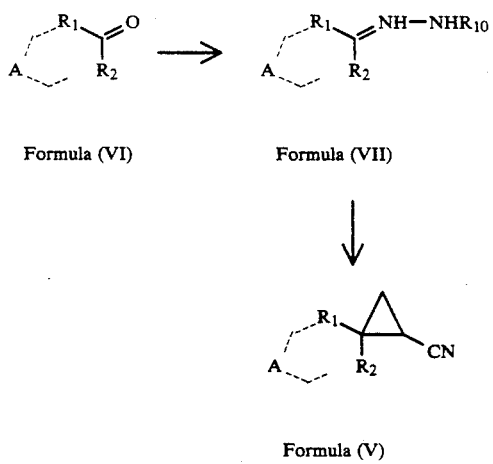

In formulae (VI) and (VII), $R_1$, $R_2$ and A are as defined above and $R_{10}$ is the hydrogen atom or a paratoluenesulfonyl group.

The hydrazones of formula (VII) which are obtained are treated with $MnO_2$ in an organic solvent such as chloroform in the case where $R_{10}$ is hydrogen, or in an alcoholate medium in the presence of pyridine if $R_{10}$ is the paratoluenesulfonyl group.

The intermediate compound is then treated with acrylonitrile in an organic solvent to give the compounds of formula (V).

The derivatives of formula (VI) are either commercially available or obtained by the conventional methods of preparing aromatic ketones, such as, for example, the Friedel-Crafts reaction.

The compounds of formula (II) are optically resolved by treatment with an optically active acid such as tartaric acid, by the procedure known to those skilled in the art.

The compounds of formula (I) as defined above, and the corresponding enantiomers and diastereoisomers and their addition salts, in particular the pharmaceutically acceptable addition salts, possess a good affinity for adenosine receptors. This affinity gives them a good activity in the central nervous system with especially analgesic properties but also anxiolytic, antidepressant and neuroprotective properties, and in the cardiovascular system with antiarrhythmic, antihypertensive and platelet aggregation inhibiting properties.

Adenosine and adenosine analogs have antinociceptives effects after systemic administration:
  H. D. VAPAATALO et al., Arzneimittelforsch., 1975, 25, 407, and
  M. T. HOLMGREN et al., J. Pharm. Pharmacol., 1983, 35, 679,
and after central administration:
  G. G. YARBOROUGH et al., Eur. J. Pharmacol., 1981, 76, 137, and
  G. E. DELANDER et al., Eur. J. pharmacol., 1987, 139, 215.

This action is probably mediated via the adenosine receptors in the spine (cf. YARBOROUGH and DELANDER, references cited above).

These properties justify the application of the derivatives of formula (I) in therapeutics and the invention further relates, by way of drugs, to the products as defined by formula (I) above, and the corresponding enantiomers and diastereoisomers and their addition salts, in particular pharmaceutically acceptable addition salts.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can be in the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic, anxiolytic, antidepressant and neuroprotective activity affording especially a favorable treatment for pain and anxiety, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a pharmaceutical composition with cardiovascular activity affording a favorable treatment for arrhythmia and hypertension and possessing platelet aggregation inhibiting properties, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. According to one embodiment, a pharmaceutical composition with analgesic and anxiolytic activity is prepared which affords especially a favorable treatment for pain and anxiety, and according to another embodiment, a pharmaceutical composition with cardiovascular activity is prepared which affords especially a favorable treatment for arrhythmia and hypertension.

According to another variant, a pharmaceutical composition is formulated as gelatin capsules or tablets containing from 5 to 300 mg of active ingredient, or as injectable preparations containing from 0.1 mg to 100 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. According to one variant of this method of treatment, the compound of formula (I), either by itself or in association with a pharmaceutically acceptable excipient, is formulated as gelatin capsules or tablets containing from 5 mg to 300 mg of active ingredient for oral administration, or as injectable preparations containing from 0.1 to 100 mg of active ingredient, or else as suppositories, ointments, creams, gels or aerosol preparations.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the afore-mentioned indications, orally in the form of tablets or gelatin capsules containing from 5 mg to 300 mg of active ingredient, or parenterally in the form of injectable preparations containing from 0.1 mg to 100 mg of active ingredient, in one or more daily administrations for an adult with an average weight of 60 to 70 kg.

In animal therapeutics, the daily dose which can be used should normally be between 0.1 and 50 mg per kg by oral administration and between 0.01 and 1 mg per kg by intravenous administration.

Further characteristics and advantages of the invention will be understood more clearly from the following description of some Examples, which in no way imply a limitation but are given by way of illustration.

EXAMPLE 1: p-Toluenesulfonohydrazide

A solution of 95 g of paratoluenesulfonyl chloride in 170 ml of THF is cooled to 4° C. A solution of hydrazine hydrate is then added dropwise, the temperature being kept at between 10° and 15° C. The mixture is allowed to return to room temperature and decanted and the organic phase is washed twice with a saturated aqueous solution of NaCl and dried. It is taken up with an equivalent volume of petroleum ether to give a white precipitate of p-toluenesulfonohydrazide.

Melting point: 110° C.

EXAMPLE 2: 4,4'-Difluorobenzophenone hydrazone

Formula (VII): $R_1=R_2=$p-fluorophenyl, A=absent, $R_{10}=H$

A mixture of 50 g of 4,4'-difluorobenzophenone, 35.5 ml of hydrazine hydrate and 200 ml of ethanol is refluxed for 8 h. It is concentrated to dryness, taken up with water and extracted with ether. The organic phase is washed with water, dried over $MgSO_4$ and then concentrated. The yellow oil obtained crystallizes slowly to give 50.6 g of 4,4'-difluorobenzophenone hydrazone.

Melting point: 78° C.

The following hydrazones of Examples 3 to 6 were prepared by the procedure of Example 2:

EXAMPLE 3: Benzophenone hydrazone

Formula (VII): $R_1=R_2=$phenyl, A=absent, $R_{10}=H$

Melting point: 98° C.

EXAMPLE 4: 3,5-Dichlorobenzophenone hydrazone

Formula (VII): $R_1=$phenyl, $R_2=$3,5-dichlorophenyl, A=absent, $R_{10}=H$

The compound, obtained in the form of an oil, is used in the crude form in the next step.

EXAMPLE 5: 3-Benzoylpyridine hydrazone

Formula (VII): $R_1=$phenyl, $R_2=$pyrid-3-yl, A=absent, $R_{10}=H$

Melting point: 130° C.

EXAMPLE 6: 9-Fluorenone hydrazone

Formula (VII): $R_1=R_2=$phenyl, A=bond, $R_{10}=H$

Melting point: 152° C.

EXAMPLE 7:

N'-[10,11-Dihydro-5H-dibenzo[a,d]cyclohepten-5-ylidene]-p-toluenesulfonohydrazide Formula (VII): $R_1 = R_2 =$ phenyl, $A = CH_2-CH_2-$, $R_{10} =$

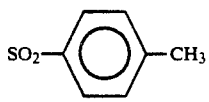

A mixture of 26.8 g of dibenzosuberone, 30 g of p-toluenesulfonohydrazide prepared in Example 1, 170 ml of ethanol and 14 ml of concentrated HCl is refluxed for 10 h.

The mixture is evaporated to dryness, taken up in chloroform and washed twice with water. The organic phase is then dried and concentrated to give 28.4 g of N'-[10,11-dihydro-5H-dibenzo[a,d]cyclohepten-5-ylidene]-p-toluenesulfonohydrazide.

Melting point: 182° C.

The following compound of Example 8 was prepared according to Example 7:

EXAMPLE 8:

N'-[5H-Dibenzo[a,d]cyclohepten-5-ylidene]-p-toluenesulfonohydrazide

Formula (VII): $R_1 = R_2 =$ phenyl, $A = CH = CH$, $R_{10} =$

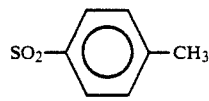

Melting point: 224° C.

EXAMPLE 9:

(±)-1,1-Di(4-fluorophenyl)-2-nitrilocyclopropane

Formula (V): $R_1 = R_2 =$ p-fluorophenyl, $A =$ absent 9 g of 4,4'-difluorobenzophenone hydrazone prepared in Example 2 are dissolved in a mixture of 90 ml of heptane and 50 ml of methylene chloride.

When total dissolution has taken place, 10.2 g of $MnO_2$ are added. The mixture is left to react for 5 h at room temperature.

It is filtered on Célite. The resulting solution is added dropwise to a mixture of 4.3 ml of acrylonitrile and 70 ml of heptane, heated to the reflux point.

The reaction mixture is refluxed for 2 h. The solvent is concentrated and the residue is taken up with isopropyl ether to give 6.6 g of (±)-1,1-di(4-fluorophenyl)-2-nitrilocyclopropane.

Melting point: 96°-99° C.

The compounds of Examples 10 to 13 were prepared by the procedure of Example 9:

EXAMPLE 10:

(±)-1,1-Diphenyl-2-nitrilocyclopropane

Formula (V): $R_1 = R_2 =$ phenyl, $A =$ absent

Melting point: 111° C.

EXAMPLE 11:

(±)-1-(3,5-Dichlorophenyl)-1-phenyl-2-nitrilocyclopropane

Formula (V): $R_1 =$ phenyl, $R_2 = 3,5$-dichlorophenyl, $A =$ absent

Melting point: 156° C.

The other pair of enantiomers, obtained in the form of an oil and purified by chromatography on silica gel (eluent: toluene), crystallizes slowly.

Melting point: 92° C.

EXAMPLE 12:

(±)-2-Nitrilo-1-phenyl-1-(pyrid-3-yl)cyclopropane

Formula (V): $R_1 =$ phenyl, $R_2 =$ pyrid-3-yl, $A =$ absent

An oil purified by chromatography on silica gel (eluent: methylene chloride 95%/acetone 5%).

EXAMPLE 13:

(±)-Spiro[cyclopropane-1,9'-[9H]-fluorene]-2-carbonitrile

Formula (V): $R_1 = R_2 =$ phenyl, $A =$ bond

The compound, obtained in the form of an oil, is purified by chromatography on silica gel (eluent:toluene).

EXAMPLE 14:

(±)-Spiro[10',11'-dihydrocyclopropane-1,5'-[5H]-dibenzo[a,d]cycloheptene]-2-carbonitrile Formula (V): $R_1 = R_2 =$ phenyl, $A = CH_2-CH_2$ 1.7 g of sodium are added to 30 ml of methanol. When the sodium methylate has formed, the methanol is evaporated off and 28.4 g of the paratoluenesulfonohydrazide derivative prepared in Example 7 and 160 ml of pyridine are added. The whole is heated at 70° for 1 h 30 min.

It is cooled, run on to crushed ice and extracted with heptane.

The organic phase is washed with water and then dried over $MgSO_4$ before being added dropwise to a mixture of 8.5 ml of acrylonitrile and 85 ml of heptane, brought to the reflux point beforehand.

The resulting mixture is refluxed until decolorization is complete.

The solvent is concentrated. The residue is cooled and the solid is filtered off to give 13.2 g of (±)-spiro[10',11'-dihydrocyclopropane-1,5'-[5H]-dibenzo[a,d]cycloheptene]-2-carbonitrile.

Melting point: 140° C.

The compound of Example 15 was obtained by the procedure of Example 14:

EXAMPLE 15:

(±)-Spiro[cyclopropane-1,5'-[5H]-dibenzo[a,d]cycloheptene]-2-carbonitrile

Formula (V): $R_1 = R_2 =$ phenyl, $A = -CH=CH-$

The compound, obtained in the form of an oil and purified by chromatography (eluent: toluene), crystallizes slowly.

Melting point: 149° C.

EXAMPLE 16:
(±)-2-Aminomethyl-1,1-di(4-fluorophenyl)cyclopropane

Formula (II): $R_1=R_2=$p-fluorophenyl, A=absent 25 g of (±)-1,1-di(4-fluorophenyl)-2-nitrilocyclopropane prepared according to Example 9 are placed in an autoclave, in the presence of Raney nickel, in a solution of 300 ml of methanol saturated with ammonia.

The whole is heated to 60° C. under a hydrogen pressure of 50 bar. It is cooled and purged with a stream of nitrogen. The catalyst is filtered off on lite and washed with methanol and the organic phase is then concentrated. The oil obtained is purified by chromatography on silica gel (eluent:chloroform 80%/methanol 20%) to give 19.8 g of (±)-2-aminomethyl-1,1-di(4-fluorophenyl)cyclopropane.

EXAMPLE 17:
(±)-2-Aminomethylspiro[cyclopropane-1,9'-[9H]-fluorene]

Formula (II): $R_1=R_2=$phenyl, A=bond 10 g of the compound obtained in Example 13 are dissolved in 200 ml of anhydrous ether. The mixture is cooled to 0° C. and 1.8 g of LiAlH$_4$ are added in portions. The resulting mixture is stirred for 1 h. The LiAlH$_4$ is hydrolyzed slowly with a mixture of 1.8 ml of water and 1.8 ml of 10% NaOH.

The reaction mixture is filtered on Célite. The material on the filter is rinsed with ether and the filtrate is extracted 3 times with 100 ml of 0.2N HCl. The combined acid phases are washed with 3 times 100 ml of ether. The solution is then rendered basic with 3.2 g of NaOH pellets. After extraction with ether, the organic phase is washed with water, dried and concentrated to give 5.4 g of (±)-2-aminomethylspiro[cyclopropane-1,9'-[9H]-fluorene] in the form of an oil, which is sufficiently pure to be used in the crude form in the next step.

The derivatives of Examples 18 to 22 were synthesized by one of the procedures of Examples 16 or 17:

EXAMPLE 18:
(±)-2-Aminomethyl-1,1-diphenylcyclopropane

Formula (II): $R_1=R_2=$phenyl, A=absent

A product obtained in the form of an oil, which is used without purification in the next step.

EXAMPLE 19:
(±)-2-Aminomethyl-1-(3,5-dichlorophenyl)-1-phenylcyclopropane

Formula (II): $R_1=$phenyl, $R_2=$3,5-dichlorophenyl, A=absent

A product obtained in the form of an oil after reduction of the compound of Example 11, which melts at 156° C.

Purification is effected by chromatography on silica gel (eluent:methylene chloride 90%/methanol 10%).

EXAMPLE 20:
(±)-2-Aminomethyl-1-phenyl-1-(pyrid-3-yl)-cyclopropane

Formula (II): $R_1=$phenyl, $R_2=$pyrid-3-yl, A=absent

An oil purified by chromatography on silica gel (eluent:chloroform 95%/isopropylamine 5%).

EXAMPLE 21:
(±)-2-Aminomethylspiro[10',11'-dihydrocyclopropane-1,5'-[5H]-dibenzo[a,d]cycloheptene]

Formula (II): $R_1=R_2=$phenyl, A=CH$_2$—CH$_2$

A product obtained in the form of an oil, which is used without further purification in the next step.

EXAMPLE 22:
(±)-2-Aminomethylspiro[cyclopropane-1,5'-[5H]-dibenzo[a,d]cycloheptene]

Formula (II): $R_1=R_2=$phenyl, A=—CH=CH—

A product obtained in the form of an oil, which is used as such.

EXAMPLE 23:
(+)-2-Aminomethyl-1,1-diphenylcyclopropane

Formula (II): $R_1=R_2=$phenyl, A=absent

A mixture of 83.6 g of 2-aminomethyl-1,1-diphenylcyclopropane prepared in Example 18, 56.3 g of L(+)-tartaric acid (99%) and 1150 ml of ethanol is refluxed for 1 h 30 min. It is filtered hot and the precipitate obtained is washed with ethanol and then ether.

The solid obtained is taken up in 1000 ml of ethanol. The mixture is heated to the boil and then filtered hot to give 26.9 g of a solid.

Melting point: 248° C.

The salt obtained in this way is taken up in water. The mixture is rendered alkaline with a solution of ammonia (28%) and then extracted with methylene chloride. The combined organic phases are dried over MgSO$_4$ and concentrated to give 20.3 g of a colorless oil. $[\alpha]_D^{27}=+76°$ (EtOH, C=1%).

This procedure is repeated several times until the optical rotation of the colorless oil obtained no longer shows appreciable variations. 16.1 g of a colorless oil of (+)-2-aminomethyl-1,1-diphenylcyclopropane are thus obtained. $[\alpha]_D^{27}=+186°$ (EtOH, C=1%).

EXAMPLE 24:
(−)-2-Aminomethyl-1,1-diphenylcyclopropane

Formula (II): $R_1=R_2=$phenyl, A=absent

The (−) isomer of 2-aminomethyl-1,1-diphenylcyclopropane is obtained by the procedure of Example 21, except that D(−)-tartaric acid (99%) is used. $[\alpha]_D^{27}=-181°$ (EtOH, C=1%).

EXAMPLE 25:
β-D-Ribofuranuronamido-1-(6-chloro-9H-purin-9-yl)-N-cyclopropyl-1-deoxy-2,3-O-(1-methylethylidene)

Formula (III): X=Cl, $R_7=$

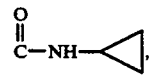

$R_8, R_9=$isopropylidene 20 g of 2',3'-O-isopropylidene-6-chloropurine-5'-uronic acid, prepared according to SCHMIDT R. R. and FRITZ H. J., Chem. Ber., 1970, 103(6), 1867-71, in 500 ml of anhydrous CHCl$_3$ stabilized with amylene, are refluxed for 5 h in the presence of 86 ml of SOCl$_2$ and 10 ml of anhydrous DMF.

The excess SOCl₂ and the solvents are distilled. The residue is taken up with 200 ml of anhydrous chloroform and added dropwise, under nitrogen, to a mixture of 150 ml of CHCl₃ and 41 ml of cyclopropylamine, cooled to 5° C. beforehand. The temperature of the reaction mixture is kept below 10° C. during the addition of the acid chloride.

The mixture is left to react for a further 30 min and then washed 3 times with a dilute HCl solution and then with a sodium bicarbonate solution. A final washing with water, followed by drying and evaporation of the solvent, gives 26.3 g of a brown oil.

Purification by chromatography on silica gel (eluent:CH₂Cl₂ 90%/acetone 10%) gives 15.7 g of β-D-ribofuranuronamido-1-(6-chloro-9H-purin-9-yl)-N-cyclopropyl-1-deoxy-2,3-O-(1-methylethylidene) in the form of an amorphous solid.

The compounds of Examples 26 to 28 were prepared by the procedure of Example 25 using the appropriate amines:

EXAMPLE 26:
β-D-Ribofuranuronamido-1-(6-chloro-9H-purin-9-yl)-1-deoxy-N-ethyl-2,3-O-(1-methylethylidene)

Formula (III): X=Cl, $R_7$=

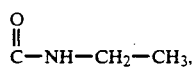

$R_8, R_9$ = isopropylidene

A yellowish oil purified by chromatography on silica gel (eluent:chloroform 95%/methanol 5%) to give a solid melting at 91° C.

EXAMPLE 27:
β-D-Ribofuranuronamido-1-(6-chloro-9H-purin-9-yl)-1-deoxy-N-(1-hydroxy-2-methylpropan-2-yl 2,3-O-(1-methylethylidene)

Formula (III): X=Cl, $R_7$=

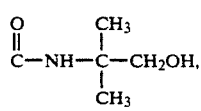

$R_8, R_9$ = isopropylidene

A brown oil purified by chromatography on silica gel (eluent:chloroform 90%/methanol 10%).

EXAMPLE 28:
β-D-Ribofuranuronamido-1-(6-chloro-9H-purin-9-yl)-1-deoxy N-isopropyl-2,3-O-(1-methylethylidene)

Formula (III): X=Cl, $R_7$=

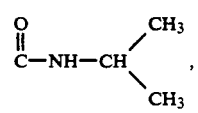

$R_8, R_9$ = isopropylidene

An orange oil purified by chromatography on silica gel (eluent:CHCl₃ 90%/acetone 10%).

EXAMPLE 29:
β-D-Ribofuranuronamido-N-cyclopropyl-1-deoxy-1-[6-[(±)-[[2-di(4-fluorophenyl)cyclopropyl]methyl]amino]-9H-purin-9-yl]-2,3-O-(1-methylethylidene)

Formula (IV): $R_1 = R_2$ = 4-fluorophenyl, A=absent, $R_7$=

$R_8, R_9$=

Under a stream of nitrogen, 4.9 g of (±)-2-aminomethyl-1,1-di(4-fluorophenyl)cyclopropane prepared in Example 16 are placed in 100 ml of ethanol. 2.8 ml of triethylamine are added, followed by 5.4 g of β-D-ribofuranuronamido-1-(6-chloro-9H-purin-9-yl)-N-cyclopropyl-1-deoxy-2,3-O-(1-methylethylidene) prepared in Example 25. The whole is refluxed for 7 h and left to stand overnight. The solvent is evaporated off and the residue is taken up with chloroform, washed with water, dried and concentrated to give 8.3 g of an amorphous solid, which is used in the crude form in the next step.

The compounds of Examples 30 to 39 were prepared in the form of amorphous solids, used as such in the next step, by following Example 29 and using one of the uronamides of Examples 25 to 28 with the appropriate amines:

EXAMPLE 30:
β-D-Ribofuranuronamido-N-ethyl-1-deoxy-1-[6-[(±)-[[2,2-diphenylcyclopropyl]methyl]amino]-9H-purin-9-yl]-2,3-O-(1-methylethylidene)

Formula (IV): $R_1 = R_2$ = phenyl, A=absent, $R_7$=

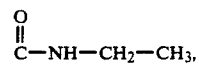

$R_8, R_9$=

EXAMPLE 31:
β-D-Ribofuranuronamido-N-cyclopropyl-1-deoxy-1-[6-[(±)-[[2,2-diphenylcyclopropyl]methyl]amino]-9H-purin-9-yl]-2,3-O-(1-methylethylidene)

Formula (IV): $R_1 = R_2$ = phenyl, A=absent, $R_7$=

$R_8, R_9 =$

EXAMPLE 32:
β-D-Ribofuranuronamido-N-cyclopropyl-1-deoxy-1-[6-[(+)-[[2,2-diphenylcyclopropyl]methyl]amino]-9H-purin-9-yl]-2,3-O-(1-methylethylidene)

Formula (IV): $R_1 = R_2 =$ phenyl, A=absent, $R_7 =$

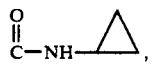

$R_8, R_9 =$

EXAMPLE 33:
β-D-Ribofuranuronamido-N-cyclopropyl-1-deoxy-1-[6-[(−)-[[2,2-diphenylcyclopropyl]ethyl]amino]-9H-purin-9-yl]-2,3-O-(1-methylethylidene)

Formula (IV): $R_1 = R_2 =$ phenyl, A=absent, $R_7 =$

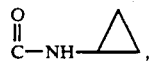

$R_8, R_9 =$

EXAMPLE 34:
β-D-Ribofuranuronamido-N-cyclopropyl-1-deoxy-2,3-O-(1-methylethylidene)-1-[6-[(±)-2-[spiro[10',11'-dihydrocyclopropane-1,5'-[5H]-dibenzo[a,d]cycloheptene]methyl]amino]-9-H-purin-9-yl]

Formula (IV): $R_1 = R_2 =$ phenyl, A=CH₂CH₂, $R_7 =$

$R_8, R_9 =$

EXAMPLE 35:
β-D-Ribofuranuronamido-N-cyclopropyl-1-deoxy-2,3-O-(1-methylethylidene)-1-[6-[(±)-2-[spiro[cyclopropane-1,9'-[9H]-fluorene]methyl]amino]-9-H-purin-9-yl]

Formula IV): $R_1 = R_2 =$ phenyl, A=bond, $R_7 =$

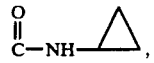

$R_8, R_9 =$

EXAMPLE 36:
β-D-Ribofuranuronamido-N-isopropyl-1-deoxy-1-[6-[(±)-[[2,2-diphenylcyclopropyl]methyl]amino]-9H-purin-9-yl]-2,3-O-(1-methylethylidene)

Formula (IV): $R_1 = R_2 =$ phenyl, A=absent, $R_7 =$

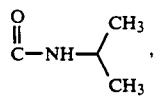

$R_8, R_9 =$

EXAMPLE 37:
β-D-Ribofuranuronamido-N-ethyl-1-deoxy-1-[6-[(+)-[[2,2-diphenylcyclopropyl]methyl]amino]-9H-purin-9-yl]-2,3-O-(1-methylethylidene)

Formula (IV): $R_1 = R_2 =$ phenyl, A=absent, $R_7 =$

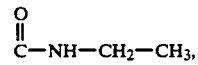

$R_8, R_9 =$

EXAMPLE 38:
β-D-Ribofuranuronamido-N-ethyl-1-deoxy-1-[6-[(−)-[[2,2-diphenylcyclopropyl]methyl]amino]-9H-purin-9-yl]-2,3-O-(1-methylethylidene)

Formula (IV): $R_1 = R_2 =$ phenyl, A=absent, $R_7 =$

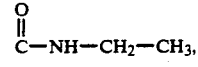

EXAMPLE 39:

β-D-Ribofuranuronamido-N-cylopropyl-1-deoxy-1-[6-[(±)-[[2-phenyl-2-(pyrid-3-yl)cyclopropyl]methyl]amino]-9H-purin-9-yl]-2,3-O-(1-methylethylidene)

Formula (IV): $R_1$=phenyl, $R_2$=pyrid-3-yl, A=absent, $R_7$=

, $R_8,R_9$=

EXAMPLE 40:

β-D-Ribofuranuronamido-N-cyclopropyl-1-deoxy-1-[6-[(±)-[[2-di(4-fluorophenyl)cyclopropyl]methyl]amino]-9H-purin-9-yl]

Formula (I): $R_1$=$R_2$=4-fluorophenyl, A=absent, $R_7$=

8.3 g of the purine obtained in Example 29 are placed in 156 ml of 1N HCl (method A). The mixture is heated at 60° C. for 3 h and neutralized with a sodium bicarbonate solution. It is extracted with chloroform and the organic phases are combined, washed with water, dried and concentrated to give 9 g of an amorphous solid.

The compound is purified by chromatography on silica gel (eluent:chloroform 95%/methanol 5%) to give 2.5 g of β-D-ribofuranuronamido-N-cyclopropyl-1-deoxy-1-[6-[(±)-[[2-di(4-fluorophenyl)cyclopropyl]methyl]amino]-9H-purin-9-yl].

Empirical formula: $C_{29}H_{28}F_2N_6O_4$.
Melting point: 157° C.
$[\alpha]_D^{27}$= −20.9° (MeOH, C=1%).

The compound of Example 40 can also be obtained by hydrolysis in a formic acid medium (250 ml of a 50% solution) with heating at 70° C. for 75 min (method B).

The compounds of Examples 41 to 50 were prepared according to Example 40 using either one of the two methods A or B:

EXAMPLE 41:

β-D-Ribofuranuronamido-N-ethyl-1-deoxy-1-[6-[(±)-[[2,2-diphenylcyclopropyl]methyl]amino]-9H-purin-9-yl]

Formula (I): $R_1$=$R_2$=phenyl, A=absent, $R_7$=

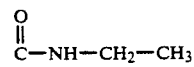

Empirical formula: $C_{28}H_{30}N_6O_4.0.22H_2O$.
Melting point: 139° C.
$[\alpha]_D^{28}$= −26.7° (MeOH, C=1%).

EXAMPLE 42:

β-D-Ribofuranuronamido-N-cyclopropyl-1-deoxy-1-[6-[(±)-[[2,2-diphenylcyclopropyl]methyl]amino]-9H-purin-9-yl]

Formula (I): $R_1$=$R_2$=phenyl, A=absent, $R_7$=

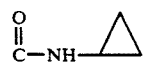

Empirical formula: $C_{29}H_{30}N_6O_4$.
Melting point: 138° C.
$[\alpha]_D^{28}$= +18.8° (MeOH, C=1%).

EXAMPLE 43:

β-D-Ribofuranuronamido-N-cyclopropyl-1-deoxy-1-[6-[(+)-[[2,2-diphenylcyclopropyl]methyl]amino]-9H-purin-9-yl]

Formula (I): $R_1$=$R_2$=phenyl, A=absent, $R_7$=

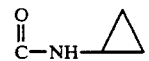

Empirical formula: $C_{29}H_{30}N_6O_4.0.8H_2O$.
Melting point: 134° C.
$[\alpha]_D^{29}$= +18.7° (MeOH, C=1%).

EXAMPLE 44:

β-D-Ribofuranuronamido-N-cyclopropyl-1-deoxy-1-[6-[(−)-[[2,2-diphenylcyclopropyl]methyl]amino]-9H-purin-9-yl]

Formula (I): $R_1$=$R_2$=phenyl, A=absent, $R_7$=

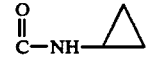

Empirical formula: $C_{29}H_{30}N_6O_4$.
Melting point: 182° C.
$[\alpha]_D^{29}$= −48.9° (MeOH, C=1%).

EXAMPLE 45:

β-D-Ribofuranuronamido-N-cyclopropyl-1-deoxy-1-[6-[(±)-2-[spiro[10',11'-dihydrocyclopropane-1,5'-[5H]-dibenzo[a,d]cycloheptene]methyl]amino]-9H-purin-9-yl]

Formula (I): $R_1$=$R_2$=phenyl, A=$CH_2CH_2$, $R_7$=

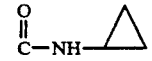

Empirical formula: $C_{31}H_{32}N_6O_4 \cdot 0.21H_2O$.
Melting point: 180° C.
$[\alpha]_D^{27} = -18.9°$ (MeOH, C=1%).

EXAMPLE 46:

β-D-Ribofuranuronamido-N-cyclopropyl-1-deoxy-1-[6-[(±)-2-[spiro[cyclopropane-1,9'-[9H]-fluorene]methyl]amino]-9H-purin-9-yl]

Formula (I): $R_1=R_2=$phenyl, A=bond, $R_7=$

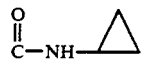

Empirical formula: $C_{29}H_{28}N_6O_4 \cdot 0.6H_2O$.
Melting point: 167° C.
$[\alpha]_D^{29} = -23.4°$ (DMSO, C=1%).

EXAMPLE 47:

β-D-Ribofuranuronamido-N-isopropyl-1-deoxy-1-[6-[(±)-[[2,2-diphenylcyclopropyl]methyl]amino]-9H-purin-9-yl]

Formula (I): $R_1=R_2=$phenyl, A=absent, $R_7=$

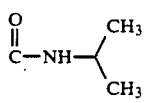

Empirical formula: $C_{29}H_{32}N_6O_4$.
Melting point: 180° C.
$[\alpha]_D^{29} = -15.4°$ (MeOH, C=1%).

EXAMPLE 48:

β-D-Ribofuranuronamido-N-ethyl-1-deoxy-1-[6-[(+)-[[2,2-diphenylcyclopropyl]methyl]amino]-9H-purin-9-yl]

Formula (I): $R_1=R_2=$phenyl, A=absent, $R_7=$

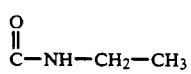

Empirical formula: $C_{28}H_{30}N_6O_4 \cdot 0.9H_2O$.
Melting point: 128°-130° C.
$[\alpha]_D^{29} = +8.8°$ (MeOH, C=1%).

EXAMPLE 49:

β-D-Ribofuranuronamido-N-ethyl-1-deoxy-1-[6-[(−)-[[2,2-diphenylcyclopropyl]methyl]amino]-9H-purin-9-yl]

Formula (I): $R_1=R_2=$phenyl, A=absent, $R_7=$

Empirical formula: $C_{28}H_{30}N_6O_4$.
Melting point: 187°-189° C.
$[\alpha]_D^{29} = -61.7°$ (MeOH, C=1%).

EXAMPLE 50:

β-D-Ribofuranuronamido-cyclopropyl-1-deoxy-1-[6-[(±)-[[2 phenyl-2-(pyrid-3-yl)cyclopropyl]methyl]amino]-9H-purin-9-yl]

Formula (I): $R_1=$phenyl, $R_2=$pyrid-3-yl, A=absent, $R_7=$

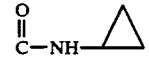

Empirical formula: $C_{28}H_{29}N_7O_4 \cdot 0.5H_2O$.
Melting point: 134° C.
$[\alpha]_D^{25} = -17.6°$ (EtOH, C=1%).

EXAMPLE 51: $N^6$-(±)-[1,1-Diphenylcyclopropan-2-yl]methyladenosine

Formula (IV): $R_1=R_2=$phenyl, A=absent, $R_7=CH_2OH$, $R_8=R_9=H$ 3.1 g of (±)-2-aminomethyl-1,1-diphenylcyclopropane prepared in Example 18 are placed in 80 ml of ethanol.

1.4 g of triethylamine and then 2 g of 6-chloroadenosine are added.

The whole is refluxed for 6 h, left to cool and concentrated. The concentrate is taken up with ethyl acetate and triturated to give 4.9 g of a white solid.

Purification by chromatography twice in succession on silica gel (chloroform 90%/methanol 10%) affords 1.4 g of $N^6$-(±)-[1,1-diphenylcyclopropan-2-yl]methyladenosine.

Empirical formula: $C_{26}H_{27}N_5O_4 \cdot 0.4H_2O$.
Melting point: 110° C.
$[\alpha]_D^{27} = -45.49°$ (MeOH, C=1%).

The compounds of Examples 52 and 53 were prepared by the procedure of Example 51:

EXAMPLE 52: $N^6$-(±)-[1-(3,5-Dichlorophenyl)-1-phenylcyclopropan-2-yl]methyladenosine Formula (IV): $R_1=$phenyl, $R_2=$3,5-dichlorophenyl, A=absent, $R_7=CH_2OH$, $R_8=R_9=H$ Empirical formula: $C_{26}H_{25}Cl_2N_5O_4$.
Melting point: 111° C.
$[\alpha]_D^{25} = -34.5°$ (MeOH, C=1%).

EXAMPLE 53: $N^6$-(±)-[Spiro[cyclopropane-1,9'-[9H]-fluoren]-2-yl]methyladenosine Formula (IV): $R_1=$phenyl, $R_2=$phenyl, A=bond, $R_7=CH_2OH$, $R_8=R_9=H$ Empirical formula: $C_{26}H_{25}N_5O_4 \cdot 0.3H_2O$.
Melting point: 160° C.
$[\alpha]_D^{29} = +4.5°$ (DMSO, C=1%).

The alcohols of Examples 51, 52 and 53 may be oxidized to the acid by reaction with an oxidizing agent such as chromium trioxide in acetone in the presence of sulfuric acid, or potassium permanganate in water in the presence of ammonia. They will subsequently give the corresponding acid chlorides after reaction with thionyl chloride and then the ribofuranuronamide derivatives of the same type as those of Examples 41, 42, 46 or 47 by reaction with appropriate amines.

PHARMACOLOGY

The pharmacological activity of the products of the Examples was evaluated by two different approaches: binding to adenosine receptors and/or demonstration of analgesic activity by the phenylbenzoquinone test.

I PROCEDURE

1. Binding to Adenosine Receptors

Principle

The affinity of the products of the Examples for the rat central $A_1$ and $A_2$ adenosinergic receptors is determined by the competitive technique using a radioactive ligand specifically bound either to the $A_1$ receptors ([$^3$H] PIA) or to the $A_2$ receptors ([$^3$H] NECA).

Method

Method of Studying the $A_1$ Receptors

Membrane Preparation

After the animal has been sacrificed by decapitation, the brain is quickly removed and washed in cold isotonic solution. The two hemispheres are separated and weighed and each of them is introduced into a polyallomer tube containing 25 volumes of cold homogenization buffer. Homogenization is effected using an Ultra-Turrax for 30 seconds (3 times 10 seconds with 10-second intervals, 70% of the maximum speed). The ground material obtained is centrifuged at 1000 g ($\approx$3000 rpm) for 10 minutes at 4° C.

The supernatant is centrifuged again at 48,000 g ($\approx$20,000 rpm) for 20 minutes at 4° C.

When this step is complete, the residue is taken up with 4 volumes of homogenization buffer, resuspended using a Vortex and homogenized with the Ultra-Turrax. Adenosine deaminase is then added at a rate of 1 U/ml, i.e. 1 µl/ml of homogenate, using a 10 µl Hamilton syringe.

After this treatment, the homogenate is shaken for 30 minutes at room temperature and then centrifuged at 80,000 g ($\approx$20,000 rpm) for 30 minutes at 4° C.

The residue obtained is resuspended in 10 volumes of homogenization buffer and passed through the Ultra-Turrax for 20 seconds (2 times 10 seconds with a 10-second interval, 70% of the maximum speed).

The homogenate prepared in this way is used for the competitive tests. It is kept at 4° C. if the studies take place the same day, or stored at $-20°$ C. in the form of 10 ml aliquots.

Competitive Test

After the homogenate has been thawed at room temperature, it is passed through a Potter homogenizer (6 manual to-and-fro movements, speed 6), diluted to 2/5 in incubation buffer and placed in a water bath thermostated at 4° C., with shaking, until the end of the experiment.

50 µl of [$^3$H] PIA at 100 nM, i.e. 2.5 nM in the final reaction medium allowing for the 1/40 dilution, and 50 µl of the product of the Example at the concentrations considered ($10^{-5}$M and $10^{-7}$M) are introduced into the reaction tubes. The reaction is initiated by the addition of 1 ml of homogenate and 900 µl of incubation buffer. The procedure is identical for all the beta-blockers studied.

The tubes are shaken and incubated in a water bath at 20° C. for 30 minutes. When the incubation is complete, the contents of the tubes are filtered on Whatman GF/B paper. Each tube is washed twice with 2 ml of rinsing buffer and then the filters themselves are rinsed with 3 ml of this same buffer.

The filters are then transferred to counting flasks and 10 ml of liquid scintillator (Ready Solv HP/b, Beckman) are added.

After they have been shaken, the flasks are stored in a refrigerator overnight and the radioactivity is then determined in a liquid scintillation counter.

3 tests are performed for each concentration studied. The non-specific binding of the [$^3$H] PIA is assessed by measuring the amount of radioactivity retained on the filter in the presence of $10^{-5}$M phenylisopropyladenosine (PIA). The value of the non-specific binding is systematically subtracted from that of the tests.

Method of Studying the $A_2$ Receptors

Membrane Preparation

After decapitation of the animal, the brain is quickly removed and washed in cold isotonic solution. The two hemispheres are separated and the striatum is removed from each of them (Bruns et al., 1986), weighed and introduced into a polyallomer tube containing 10 volumes of cold homogenization buffer. The tissue is homogenized with an Ultra-Turrax for 30 seconds (3 times 10 seconds with 10-second intervals, 70% of the maximum speed). The ground material is centrifuged at 50,000 g ($\approx$20,500 rpm) for 10 minutes at 4° C.

The residue obtained is resuspended in 10 volumes of homogenization buffer using a Vortex and homogenized with the Ultra-Turrax (5 to 10 seconds, 70% of the maximum speed).

Adenosine deaminase is then added at a rate of 1 U/ml, i.e. 1 µl/ml of homogenate, using a 10 µl Hamilton syringe. The homogenate treated in this way is shaken at room temperature for 30 minutes.

When the incubation is complete, the homogenate is centrifuged at 50,000 g ($\approx$20,500 rpm) for 10 minutes at 4° C.

The residue is taken up with 5 volumes of cold homogenization buffer and passed through the Ultra-Turrax (2 times 10 seconds with a 10-second interval, 70% of the maximum speed) and the homogenate prepared in this way is finally frozen at $-70°$ C.

Competitive Test

After the homogenate has been thawed at room temperature, 15 volumes of incubation buffer are added. The homogenate is shaken on a Vortex, passed through a Potter homogenizer (6 to-and-fro movements, speed 6), diluted to 1/10 in incubation buffer and finally placed in a water bath thermostated at 4° C., with shaking, until the end of the experiment.

50 µl of [$^3$H] NECA at 160 nM, i.e. 4 nM in the final reaction medium allowing for the 1/40 dilution, and 50 µl of the product of the Example at the concentrations considered ($10^{-5}$M and $10^{-7}$M) are introduced into the reaction tubes. The reaction is initiated by the addition of 1 ml of homogenate and 900 µl of incubation buffer. The procedure is similar for all the compounds studied.

The tubes are shaken and incubated in a water bath at 25° C. for 60 minutes. When the incubation is complete, the contents of the tubes are filtered on Whatman GF/B paper. Each tube is washed twice with 2 ml of rinsing buffer and then the filters themselves are rinsed with 3 ml of this same buffer before being transferred to counting flasks.

10 ml of liquid scintillator (Ready Solv HP/b, Beckman) are added to all the flasks. These are shaken and stored in a refrigerator overnight. The radioactivity is determined in a liquid scintillation counter.

3 tests are performed for each concentration studied. The non-specific binding of the [³H] NECA is determined by measuring the amount of radioactivity retained on the filter in the presence of 5 μM N-ethylcarboxamidoadenosine (NECA). The value of the non-specific binding is systematically subtracted from that of the tests.

Treatment Of The Data

The results are expressed for each product in the form of the percentage displacement (n=3) of the labeled radioligand at concentrations of $10^{-5}M$ and $10^{-7}M$.

2. Phenylbenzoquinone Test

Method

The intraperitoneal injection of phenylbenzoquinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the Examples are administered orally one hour before the injection of phenylbenzoquinone.

The stretching and twisting movements are counted for each mouse over an observation period of 5 minutes.

II RESULTS

The results of the experiments demonstrate the affinity of the products of the Examples for adenosine receptors and their analgesic properties are presented in Tables 1 and 2 respectively.

III TOXICOLOGY

The tolerance of the products of the Examples was assessed in rats after oral administration. It was found to be good up to a dose of 100 mg/kg.

IV CONCLUSION

The products of the Examples described in the present invention possess particularly valuable analgesic properties, whose original mechanism of action results from an interaction with adenosine receptors.

TABLE 1

| Product of | % displacement of the labeled ligand | | | |
|---|---|---|---|---|
| | A1 | | A2 | |
| | 1E-5M | 1E-7M | 1E-5M | 1E-7M |
| Example 40 | 94 | 15 | 89 | 53 |
| Example 41 | 98 | 31 | 100 | 68 |
| Example 42 | 96 | 20 | 94 | 59 |
| Example 43 | 97 | 44 | 96 | 73 |
| Example 44 | 90 | 10 | 100 | 19 |
| Example 45 | 93 | 20 | 79 | 12 |
| Example 46 | — | — | 92 | 38 |
| Example 47 | 93 | 7 | 84 | 17 |
| Example 48 | 99 | 54 | 92 | 71 |
| Example 49 | 93 | 15 | 86 | 0 |
| Example 51 | 93 | 18 | 95 | 56 |
| Example 52 | 92 | 18 | 92 | 28 |

TABLE 2

| Product of | Phenylbenzoquinone test 50% inhibitory dose mg/kg p.o. |
|---|---|
| Example 40 | 0.5 |

TABLE 2-continued

| Product of | Phenylbenzoquinone test 50% inhibitory dose mg/kg p.o. |
|---|---|
| Example 41 | 0.5 |
| Example 42 | 0.9 |
| Example 43 | 1.2 |
| Example 44 | ≈1 |
| Example 45 | 1.6 |
| Example 46 | 0.6 |
| Example 47 | 2 |
| Example 48 | 0.3 |
| Example 49 | 0.7 |
| Example 51 | 31 |
| Example 52 | 41 |

What is claimed is:

1. An adenosine compound of the formula

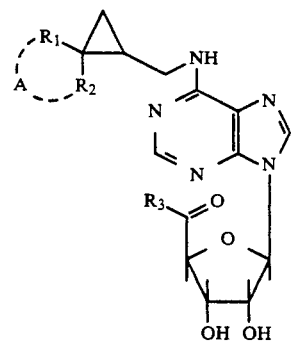

and pharmaceutically acceptable addition salts thereof, in which:

$R_1$ and $R_2$ are identical or different, and represent an aromatic ring selected from the group consisting of a phenyl radical which is unsubstituted, monosubstituted or polysubstituted by a halogen atom, and a pyridyl radical, wherein A may be absent or may be selected from the group consisting of a single bond, a CH=CH group or a $CH_2$—$CH_2$ group;

$R_3$ is a group $NHR_4$, in which $R_4$ is a hydrogen atom, an alkyl radical having 1 to 6 carbon atoms, a $C_3$-$C_7$ cycloalkyl radical, or an alkyl radical having 1 to 6 carbon atoms of which one of the hydrogen atoms is substituted by one hydroxyl group.

2. A compound according to claim 1, which is selected form the group consisting of:

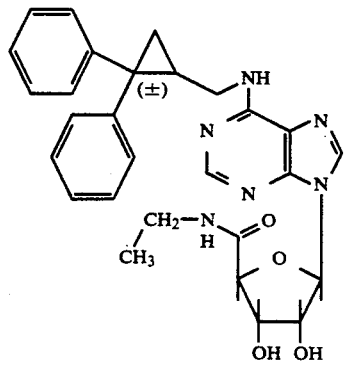

-continued

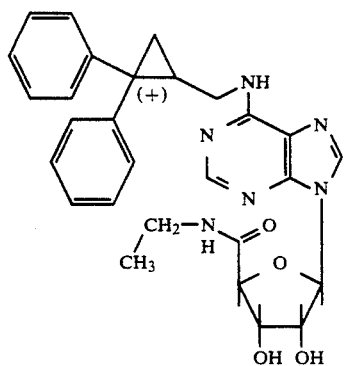

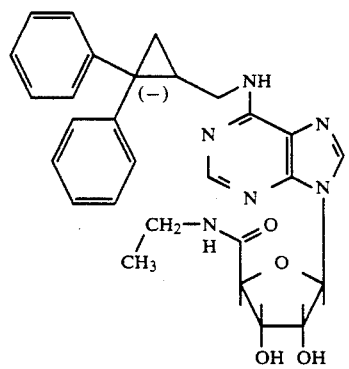

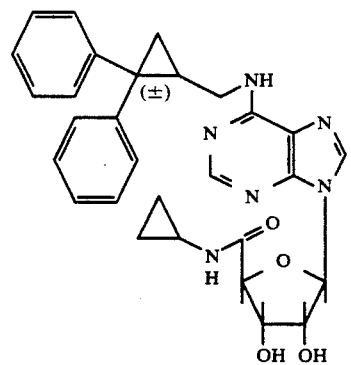

-continued

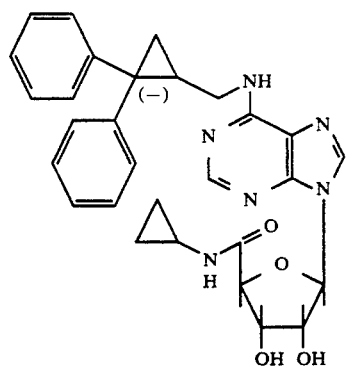

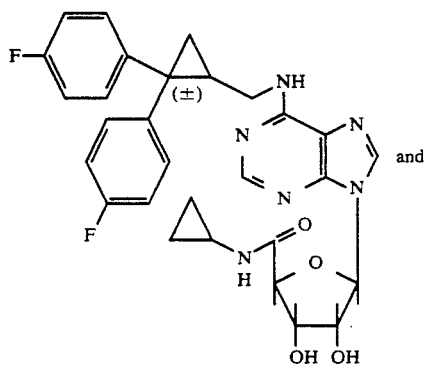

and

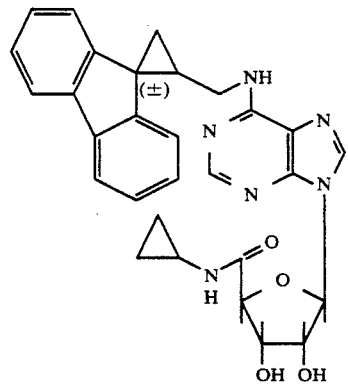

3. A compound according to claim 1 wherein $R_1$ is the phenyl group.

4. A compound according to claim 1 wherein $R_2$ is the phenyl group.

5. A compound according to claim 1 wherein $R_1$, $R_2$ and A are the 9-fluorenyl radical ($R_1$=phenyl; $R_2$=phenyl; A=bond).

6. A compound according to claim 1 wherein $R_3$ is an N-cyclopropylamine radical or an N-ethylamine radical.

7. A compound according to claim 1, wherein said pyridyl radical is a pyrid-3-yl radical.

8. A pharmaceutical composition which comprises a pharmaceutically effective amount of a compound of formula (I) as defined in claim 1, or one of its pharmaceutically acceptable addition salts together with a pharmaceutically acceptable excipient, vehicle or carrier.

* * * * *